Figure 1:
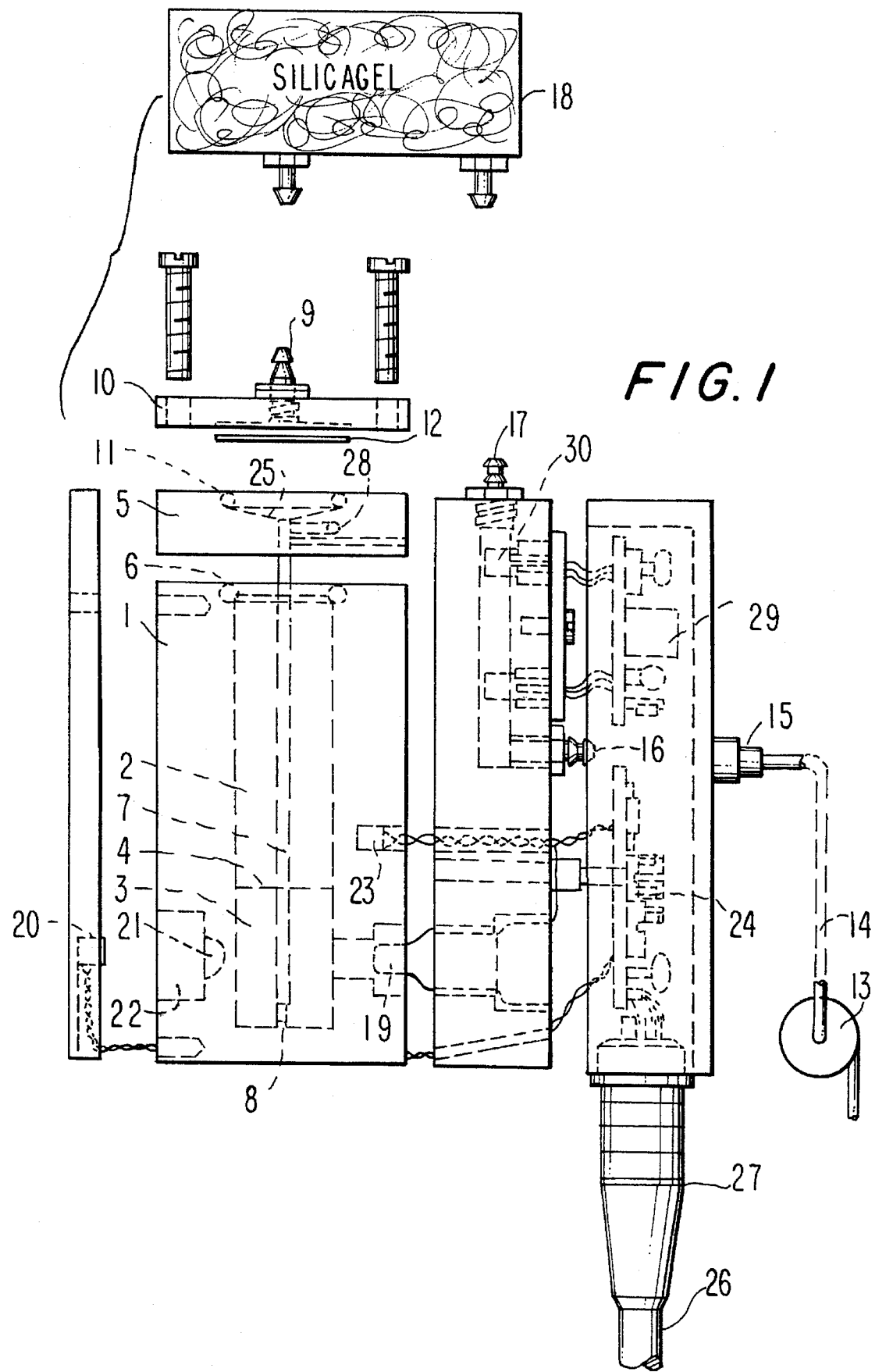

United States Patent [19]

Saugmann et al.

[11] Patent Number: 5,514,562
[45] Date of Patent: May 7, 1996

[54] METHOD AND AN APPARATUS FOR CURRENTLY MEASURING THE PRESENCE OF TRACES OF AN UNDESIRABLE SUBSTANCE IN AIR

[75] Inventors: Grethe Saugmann, Kalundborg; Johannes Poulsen, Farum; Bjarne Bøving, Alleroed; Mads Christian Hage Nielsen, Brønshoj, all of Denmark

[73] Assignee: Novo Nordisk A/S

[21] Appl. No.: 318,569

[22] Filed: Oct. 5, 1994

Related U.S. Application Data

[63] Continuation of Ser. No. 98,282, Aug. 4, 1993, abandoned.

[30] Foreign Application Priority Data

Feb. 7, 1991 [DK] Denmark .................. 209/91

[51] Int. Cl.[6] .............. C12M 1/34; C12Q 1/37; G01N 21/51; G01N 21/75
[52] U.S. Cl. .............. 435/23; 73/31.02; 435/807; 435/808; 435/288.7; 435/287.1; 436/167
[58] Field of Search .............. 435/23, 24, 291, 435/313, 807, 808; 73/31.01, 31.02; 436/34, 167, 168

[56] References Cited

U.S. PATENT DOCUMENTS

| | | | |
|---|---|---|---|
| 3,542,515 | 11/1970 | Scott | 435/808 |
| 3,715,298 | 2/1973 | Goodson et al. | 435/291 |
| 3,962,041 | 6/1976 | Muller et al. | 425/291 |
| 4,489,164 | 12/1984 | McConnaughey et al. | 436/130 |
| 4,586,389 | 5/1986 | Vincent et al. | 73/863 |
| 4,617,277 | 10/1986 | Bohl | 436/34 |
| 4,766,080 | 8/1988 | Fleming | 436/74 |
| 5,250,418 | 10/1993 | Moller et al. | 436/177 |

FOREIGN PATENT DOCUMENTS

| | | |
|---|---|---|
| 0092246 | 10/1983 | European Pat. Off. . |
| 0258862 | 3/1988 | European Pat. Off. . |
| 0272407 | 6/1988 | European Pat. Off. . |
| 3729189A1 | 3/1988 | Germany . |

*Primary Examiner*—Jeffrey E. Russel
*Attorney, Agent, or Firm*—Steve T. Zelson; James J. Harrington

[57] ABSTRACT

A method for measuring the presence of traces of substance in air by providing in a cuvette a substrate reacting with the substance by changing its opacity, passing at a defined flow rate air from the air body to be checked through the substrate, measuring the development of opacity. A portable apparatus comprises a housing (1, 101) holding a cuvette (131) containing a substrate (3, 103), an inlet tube (28) leading to the bottom of the cuvette, a pump (13) sucking air from the cuvette through a flow monitor (138) controlling the pump, a spectrophotometer lamp (19, 119) and a photodiode (20) on opposite sides of the cuvette (131), a monitor monitoring the level (4, 104) of the substrate in the cuvette, and a monitor (23, 123) monitoring the temperature of the substrate, a computer (24) receiving signals from the photodiode (20), the level monitor, and the temperature monitor to calculate a temperature and level compensated indication of the substrate opacity.

9 Claims, 2 Drawing Sheets

ID NO:1) as the substrate the
METHOD AND AN APPARATUS FOR CURRENTLY MEASURING THE PRESENCE OF TRACES OF AN UNDESIRABLE SUBSTANCE IN AIR This application is a continuation application of application Ser. No. 08/098,282, filed Aug. 4, 1993, now abandoned, the contents of which are incorporated herein by reference.

The invention relates to measuring the presence of traces of undesirable substances in air.

For environmental reasons many substances are undesirable in the air which people have to breath or stay in by working. Such substances may e.g. be toxic or allergenic or in other ways injurious to the health. Consequently, the legal levels of the presence of such substances are set extremely low making it difficult even to check if these levels are exceeded.

According to a known method for checking the content of noxious substances in the air a stationary device is used sucking through a filter a considerable amount of the air to be checked. After some time the filter may be replaced by a new one and the dust collected on the first mentioned filter may be analyzed for undesirable substances. When the amount of air pumped through the filter is known the analysis may reveal an average of the content of noxious substances during the time the filter has been used. This will give no safe indication of whether the legal level has been heavily exceeded for a short time, but well obeyed for most of the time.

The above solution only allows the air at a certain locality to be checked. In fact the solution needed has to check the air surrounding a working person wherever he goes and for this purpose U.S. Pat. No. 4,586,389 suggests a portable aerosol dust spectrometer comprising a powerful pump for sucking in about 10 l of air per minute. The dust in the air is sorted according to grain size and deposited on sticky drums driven by a clock work. This makes it possible to analyze how the dust load has been through the day.

However, what is wished for is a measuring method and a device not only allowing the device to be carried by the working person but also to immediately analyze the air sample sucked in by the device thereby allowing an immediate alarm if the legal level is exceeded.

It is the object of the invention to provide a method for practically continuously measuring very small amounts of a given substance in the air. Further, the object is to provide a portable apparatus for carrying out this method.

The method according to the invention comprises the steps mentioned in claim 1. A sample of the air body to be checked is led through the substrate causing a change in the opacity of this substrate and the development of this opacity is detected. This provides a practically continuous monitoring of the opacity and consequently of the substance load as the flow of the air sample must only be stopped for a short time to prevent air bubbles from impairing the opacity measurement.

The extreme high sensibility of this method further enables that the air flow is held as low as about 0.3 l per minute. This enhances the portability as this lower air flow not only allows smaller dimensions of the air passages, but also a smaller pump capacity and consequently a smaller power supply.

If a substrate is used which reacts catalytically with the substance changing its opacity at a rate proportional to the amount of substance a still more sensitive method of measuring is obtained as an amount of substance which would not be able to immediately change the opacity to a measurable extent by working catalytically will on a long view cause a measurable opacity.

Using a substrate reacting catalytically with the substance, the opacity development rate must be measured to decide on possible increase in this rate from one time interval to another, an increase indicating that more of the substance has been added to the substrate. The opacity development rate may be detected by differentiation of the opacity/time-function. The first derivative will indicate the cumulative substance load and the second derivative will indicate the immediate substance load, i.e. the substance load during the last time interval. Using Suc-Ala-Ala-Pro-Phe-p-Nitroanilid (SEQ ID NO:1) as the substrate the method may be used for detecting traces of protease in the air.

An apparatus for carrying out the method may be designed as stated in claim 4. To make it portable such an apparatus must be miniaturized and at least the cuvette with the air intake must be placed practically on the spot where the sample of the air body is taken to prevent substance from being sedimented in tubings before it reaches the substrate in the cuvette.

As a part of the miniaturization the inlet tube may constitute an electrode of a capacitive level monitor, the inner wall of the cuvette holding housing constituting the other electrode.

The cuvette may be upwards closed by a hydrophobic filter, through which filter air is sucked from the upper part of the cuvette. This filter prevents aerosol generated by the air bubbling through the substrate from leaving the cuvette.

A lens and a filter may be mounted in front of the photometer diode, the lens to unify the light passing through the cuvette, and the filter to ensure that only the wave length at which the opacity changes is most well defined is taken into consideration whereby opacity contribution from other reactions are eliminated.

To prevent moisture from evaporated substrate from damaging the air flow monitor, which is inserted in the air passage receiving the air leaving the cuvette, a moisture absorber may be inserted in the air passage between the cuvette and the flow monitor.

The portability is enhanced by the fact that the power supply, the pump, and the computer may be separated from the rest of the apparatus being connected to this rest of the apparatus through cables and tubings. A special waistcoat with pockets and belts to carry the individual parts of the apparatus may be manufactured.

Figure 2:
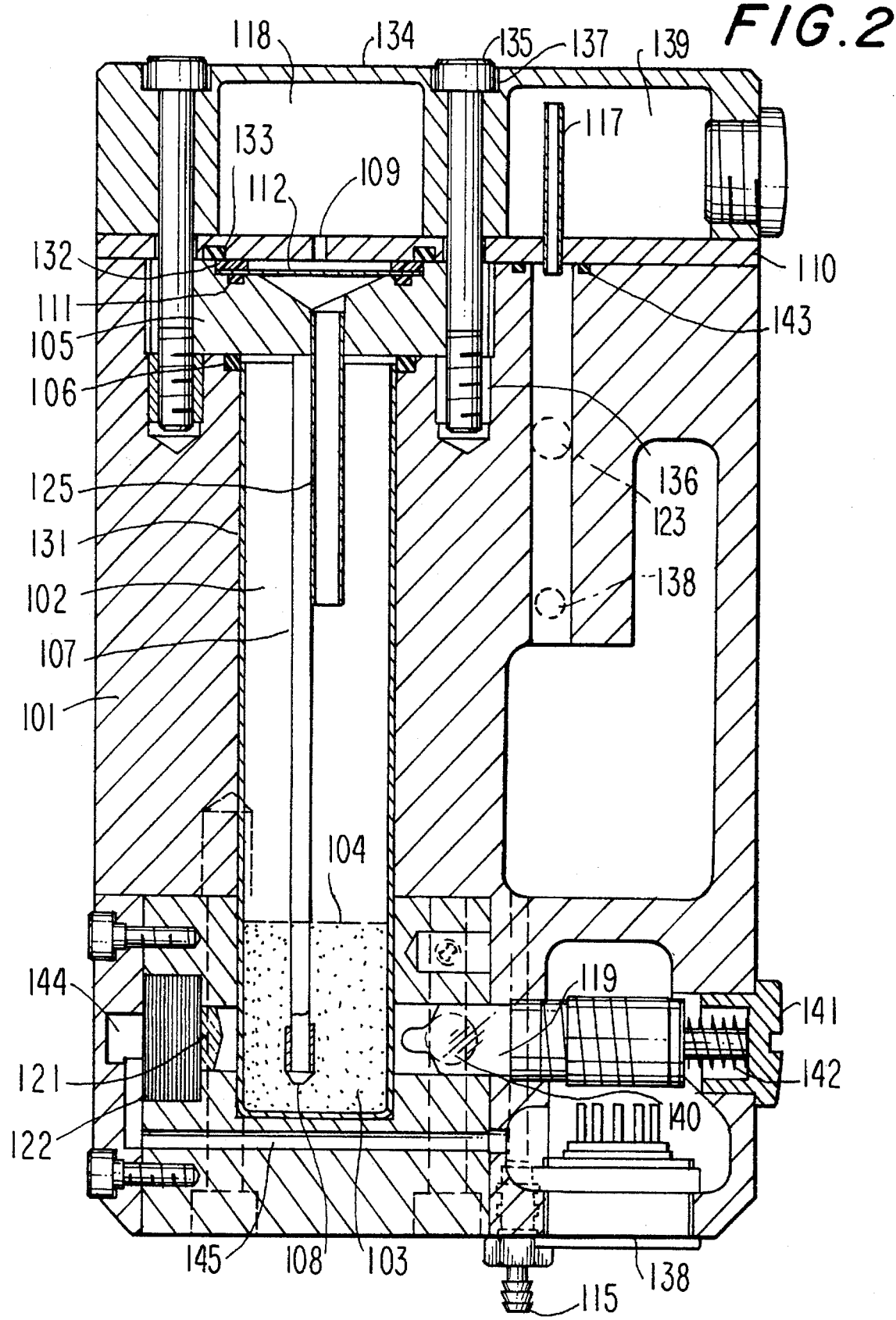

In the following the invention is described in further details with reference to the drawings, wherein FIG. 1 shows schematically the construction of an apparatus according to the invention, and FIG. 2 shows a sectional view of a commercial, integrated construction of the apparatus.

The apparatus schematically shown comprises a housing 1 holding a cuvette with a chamber 2 in which a substrate 3 is filled to the level 4. The chamber 2 is at its top provided with a cover 5 sealed to the cuvette body by an O-ring 6. Secured to the cover 5 is a tube 7 which extends along the longitudinal axis of the chamber 2 when the cover 5 is mounted on the housing 1. The tube 7 at its upper end has an inlet 28 opening into the surrounding air body, which should be checked, and is at its lower end provided with a nozzle 8 through which air sucked through the tube 7 emits and bubbles through the substrate 3.

The suction of air through the tube 7 is obtained by providing a vacuum in the chamber 2 above the substrate. This vacuum is obtained by sucking air from the chamber through a suction nipple 9 in a closing plate 10 sealed to the cover 5 by another O-ring 11 with a hydrophobic filter 12 placed between the suction nipple 9 and the top of the chamber 2 which filter having a pore diameter of e.g. 0.5μ should prevent aerosol formed when air bubbles through the substrate from being entrained by the air out of the cuvette. Drops caught by the filter will at least when the pump is stopped drop into the funnel 25 and flow back into the cuvette.

The suction is provided by a pump 13 which may be placed outside the measuring part of the apparatus and be connected to this part by a tubing 14 which by a snap coupling 15 may be coupled to the measuring part. In the measuring part the air is sucked through a flow monitoring device having an inlet nipple 16 and an outlet nipple 17, the first for being connected to the nipple 9 at the top of the cuvette, and the other for being connected to the snap coupling 15 and consequently to the suction side of the pump 13.

The flow monitoring device comprising a pair of sensors 30 in the air passage and an computer interface 29 is designed to control the pump motor to provide a constant air flow through the apparatus, or it may monitor the actual flow so that variations may be compensated for when the substance load is calculated.

As mentioned, the inlet nipple 16 of the air flow monitor is connected to nipple 9 at the top of the cuvette. As the air leaving the cuvette is saturated with moisture due to the fact that the air has been bubbled through the substrate, this moisture is removed by establishing the connection through a vessel 18 with a moisture absorbing agent e.g. silica gel.

A spectrophotometer lamp 19 at one side of the cuvette chamber 2 lights through the substrate and the light passing the substrate is measured by a photo-diode 20 placed on the opposite side of the chamber opposite the lamp 19. A lens 21 is provided in front of the photo-diode 20 to unify the light and a filter 22 is inserted between the lens 21 and the photo-diode 20 to selectively provide a measuring of the light wave length at which the opacity is chiefly influenced.

Further, a temperature sensor 23 is provided to monitor the temperature of the substrate making it possible to take into account the fact that the reaction in the substrate is temperature dependent. Similarly, the level of the substrate is currently monitored as the opacity of the substrate will vary when it becomes more concentrated due to evaporation when air is bubbled through it. Signals from the temperature and level monitors and from the photo-diode are led to a computer interface 24. A not shown computer may perform all necessary calculations on the basis of signals obtained from the different measuring and monitoring devices. Further, the computer may store calculated data in preparation of a later read out of such data.

When being used the measuring part of the apparatus, the pump, the computer, and the power supply may be carried in different pockets or clipped to belts to distribute the weight over the body of the carrying person, the measuring part being connected to the suction side of the pump 13 by a tubing 14 and to the power supply and the computer by a cable 26 connected to the measuring part by a plug 27.

In FIG. 2 parts corresponding to parts in FIG. 1 carry the same references only with the prefix "1".

The housing 101 accommodates a cuvette 131 forming a chamber 102 into which a substrate 103 is filled to a level 104.

A cover 105 is sealed to the cuvette 131 by an O-ring 106. A tube 107 extends longitudinally in the chamber 102 with its lower end immersed into the substrate 103. This lower end is provided with a nozzle 108 whereas the other not visible end of the tube 107 forms an inlet for the air to be checked.

The vessel containing silicagel is integrated as a chamber 118 in a lid 134. Thereby the nipple 9 in FIG. 1 may be replaced by an opening 109 in a closing plate 110, which is sealed to the cover 105. This sealing is obtained by a silicone O-ring 111 forming a sealing between the cover 105 and a hydrophobic filter 112, which filter by a PTFE ring 132 is held in abutment with the upper side of the O-ring 111. A silicone gasket 133 in a recess in the closing plate 110 seals against the PTFE ring 132 and the cover 105. Liquid detained by the hydrophobic filter 112 is lead back into the cuvette by a funnel having a spout 125 depending from the cover 105 into the cuvette.

The lid 134 is secured to the housing 101 by screws screwed into a threaded bushing 136 in the housing 101 and a spring washer 137 is provided beneath the head 135 of the screw.

Air is sucked through the apparatus by a not shown pump which by a not shown tubing is coupled to a nipple 115 placed adjacent to a socket 128 to which an electric cable may be coupled by a plug corresponding to the plug 27 in FIG. 1. An inlet tube 117 to a flow monitor 138, which monitor is just indicated and not shown in details as in FIG. 1, is mounted in the closing plate 110 and opens into another chamber 139 in the lid 134. The chamber 139 communicates through a not shown duct with the chamber 118. A sealing O-ring 143 surrounding the inlet tube 117 is provided between the closing plate 110 and the housing 101.

The photometer part comprises a spectrophotometer lamp 119 at one side of the cuvette 131 and a photodiode opposite the lamp at the other side of the cuvette 131. A lens 121 and a filter 122 are mounted in front of the not shown photodiode, which may be mounted in a chamber 144 with its electric leads passed through a duct 145 to the inner ends of electric terminals in the socket 128.

Adjacent to the lamp 119 a reference light sensor 140 is mounted to monitor the light output from the lamp to make the computer compensate for reduced light output or to make an indication that the lamp has burned out and has to be replaced. Such replacement may easily be made by unscrewing a plug 141 behind the lamp, removing the lamp, and replacing it by a new one which is pressed into position by a spring 142 when the plug is again screwed into the housing.

As appears, the electric components and their lead connections are not shown in FIG. 2, but their positions are indicated. In this way is indicated a temperature sensor 123 measuring the temperature of the housing, which temperature as a result of the excellent heat conductivity of this housing corresponds to the temperature of the substrate 103.

The cuvette chamber is filled to a predetermined level with a substrate reacting with the substance, the presence of which should be checked for by making this substrate coloured or more opaque. A substrate is chosen which reacts catalytically with the substance, i.e. the rate of colouring and not the total colouring is proportional to the amount of the substance, or put in another way, when a particle of the substance enters the substrate this will not cause a defined colouring of this substrate corresponding to the amount of substance in the particle, but it will start a colouring of the substrate which colouring will be intensified until the substrate has reached its maximal colouring, the rate at which this colouring is intensified being proportional to the amount of substance. This way a particle of the substance how small it ever is will cause a colouring of the substrate making this method of measuring extremely sensitive.

In principle, the apparatus performs a continuous checking of the air, but for practical reasons it is necessary to stop the pump at intervals to provide a measuring as the bubbles would disturb the function of the spectrophotometer measuring. Comparing the progress of the colouring in one time interval with the progress during the preceding interval it is possible to decide whether a new substance has been added to the substrate as the progress of the colouring will then be quicker. If a graph of the opacity as a function of time is plotted, it will be constituted by pieces of lines, the slopes of which indicate the total amount of substance in the substrate, and a change in slope indicates the addition of further substance. Consequently, the second derivative of the opacity/time graph expresses the immediate load of substance in the air checked.

The above consideration is valid for a constant amount of substrate in the cuvette having a fixed temperature. As mentioned, the liquid of the substrate will evaporate and leave the cuvette with the air and consequently the substrate will become more dense and for this reason the opacity will increase. By constantly monitoring the level of the substrate the level signals from the level monitor may make the computer compensate for variations in opacity caused by the enrichment of the substrate. Correspondingly, the computer may receive a temperature signal to compensate for the fact that the reaction rate varies with the temperature. This way the computer may currently calculate the concentration of substance, e.g. enzymes in the air bubbling through the cuvette chamber.

The apparatus may now be equipped with different alarms. To make the apparatus fulfil its purpose, an alarm may indicate that the substance load of the air is higher than accepted, this being indicated by the second derivative of the opacity/time function exceeding a preset value.

However, it is important to provide other alarms which indicate malfunctions of the apparatus. Such malfunctions may be that the flow control cannot establish the wanted flow, that the substrate in the cuvette has achieved its maximal colouring, that the substrate level is too low, that the batteries are almost discharged, that the photometer lamp is burned out, or that the reaction speed in the substrate has reached its maximum.

Signals which the computer may interpret as indications of malfunctions may be obtained from different sensors. Obviously the signal from the level monitor may indicate if the level is too low. Correspondingly, the signal from the photo-diode may indicate whether the substrate has become too opaque, or whether the lamp is burned out. The pump controlling circuit reaching the limits of its control field will indicate air flow failure and a voltage monitor may indicate whether the batteries are almost discharged. When the reaction speed has reached its known maximum it may be indicated by the first derivative of the opacity/time graph reaching its maximum.

We claim:

1. A method for currently measuring the presence of traces of an undesirable substance in air, comprising the steps, a. providing in a cuvette a known amount of a substrate reacting catalytically with the undesireable substance changing the opacity of the substrate at a rate proportional to the amount of the undesirable substance, b. measuring the temperature and the level of the substrate in the cuvette, c. passing at a defined flow rate air from the air to be checked through the substrate, d. measuring at preset time intervals the opacity of the substrate, e. comparing the opacity development during the latest time interval with the development of opacity during the preceding time interval, f. calculating the opacity development rate to decide whether this rate taken with the compensation for variations in temperature and level of substrate has increased from one time interval to another, taking an increase in opacity development rate as indicating that more of the undesirable substance has been added to the substrate.

2. A method according to claim 1, characterized in, that the calculation of the opacity development rate is obtained by differentiation of a function expressing the opacity as a function of the time in which function compensations are made for variations in temperature and level of the substrate, taking the first derivative as an indication of the cumulative undesirable substance load, and the second derivative as an indication of the immediate undesirable substance load.

3. A method according to claim 1, characterized in, that the substrate is Suc-Ala-Ala-Pro-Phe-p-Nitroanilid (SEQ ID NO:1) for detecting protease.

4. A portable apparatus for carrying out the method according to claim 1, characterized in, that it comprises a housing (1;101) holding a cuvette (31;131) containing an amount of the substrate (3;103) reacting catalytically with the undesirable substance changing the opacity development rate of this substrate (3;103), an inlet tube (7;107) leading from the air to be checked to the near bottom of the cuvette (31;131), an air pump (13) sucking air from the upper end of the cuvette (31;131) through a flow monitor (29,30;138) controlling the pump (13) to provide a preset constant air flow through the apparatus, a spectrophotometer lamp (19;119) and a photo-diode (20) placed opposite each other on opposite sides of the cuvette (31;131), a level sensor monitoring the level (4;104) of the substrate in the cuvette (31;131), and a temperature sensor (23;123) monitoring the temperature of the substrate, a computer interface (24) receiving signals from the photo-diode (20), the level sensor, and the temperature sensor (23;123) to calculate a temperature and level compensated indication of the opacity of the substrate (3;103).

5. An apparatus according to claim 4, characterized in, that the inlet tube constitutes an electrode of a capacitive level monitor, the inner wall of the housing (1;101) constituting the other electrode.

6. An apparatus according to claim 5, characterized in, that the cuvette (31;131) is upwards closed by a hydrophobic filter (12;112), through which filter air is sucked from the upper part of the cuvette (31).

7. An apparatus according to claim 4, characterized in, that a lens (21;121) and a filter (22;122) are mounted in front of the photo-diode (20).

8. An apparatus according to any of the claim 4, characterized in, that a moisture absorber (18;118) is inserted in the air passage between the cuvette (31;131) and the flow monitor (29,30;138).

9. An apparatus according to claim 4, characterized in, that a power supply, the pump (13), and a computer are separated from the rest of the apparatus and are connected to this rest of the apparatus through cables (26) and tubings(14).

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( x i ) SEQUENCE DESCRIPTION: SEQ ID NO:1:

```
Xaa Ala Ala Pro Phe
1               5
```